(12) United States Patent
Maule et al.

(10) Patent No.: US 10,108,003 B2
(45) Date of Patent: *Oct. 23, 2018

(54) SYSTEMS AND METHODS FOR PROVIDING MONITORING STATE-BASED SELECTABLE BUTTONS TO NON-DESTRUCTIVE TESTING DEVICES

(71) Applicant: General Electric Company, Schenectady, NY (US)

(72) Inventors: Bryan David Maule, Camillus, NY (US); Thomas Charles Ward, Auburn, NY (US); Melissa Rose Stancato, Syracuse, NY (US)

(73) Assignee: General Electric Company, Schenectady, NY (US)

( * ) Notice: Subject to any disclaimer, the term of this patent is extended or adjusted under 35 U.S.C. 154(b) by 428 days.

This patent is subject to a terminal disclaimer.

(21) Appl. No.: 14/292,651

(22) Filed: May 30, 2014

(65) Prior Publication Data

US 2015/0350639 A1 Dec. 3, 2015

(51) Int. Cl.
*G02B 23/24* (2006.01)
*H04N 17/00* (2006.01)
(Continued)

(52) U.S. Cl.
CPC ....... *G02B 23/2484* (2013.01); *G06F 3/0481* (2013.01); *G06F 3/0482* (2013.01);
(Continued)

(58) Field of Classification Search
CPC .................................................. G02B 23/2484
See application file for complete search history.

(56) References Cited

U.S. PATENT DOCUMENTS

2002/0054224 A1* 5/2002 Wasula ................ H04N 1/2112
348/231.6
2005/0088525 A1* 4/2005 Stavely .............. H04N 1/00127
348/207.1
(Continued)

OTHER PUBLICATIONS

U.S. Appl. No. 14/292,771, filed May 30, 2014, Goldberger.
(Continued)

*Primary Examiner* — William Bashore
*Assistant Examiner* — Nathan Shrewsbury
(74) *Attorney, Agent, or Firm* — Mintz Levin Cohn Ferris Glovsky and Popeo, P.C.

(57) ABSTRACT

A system includes a portable non-destructive testing (NDT) device. The NDT device includes a processor configured to receive imaging data captured via a sensor of the NDT device, cause a display of the NDT device to display an image to be analyzed based on the imaging data, and cause the display to display a graphical user interface (GUI). The GUI includes a first plurality of user-selectable objects. Each of the first plurality of user-selectable objects is configured to activate one or more monitoring functions of the NDT device. The processor is also configured to cause the display to display at least a first set of the first plurality of user-selectable objects. The first set of the first plurality of user-selectable objects is configured to substantially overlay the image. The first set of the first plurality of user-selectable objects is displayed based at least in part on an inspection state of the NDT device.

19 Claims, 13 Drawing Sheets

(51) Int. Cl.
  *G06F 3/0484* (2013.01)
  *G06F 3/0481* (2013.01)
  *G06F 3/0488* (2013.01)
  *G06F 3/0482* (2013.01)
  *A61B 1/00* (2006.01)

(52) U.S. Cl.
  CPC ........ *G06F 3/0488* (2013.01); *G06F 3/04842* (2013.01); *G06F 3/04886* (2013.01); *H04N 17/002* (2013.01); *A61B 1/0005* (2013.01); *A61B 1/00039* (2013.01)

(56) References Cited

U.S. PATENT DOCUMENTS

| | | | | |
|---|---|---|---|---|
| 2005/0264796 | A1* | 12/2005 | Shaw | G01B 11/162 356/237.2 |
| 2006/0274885 | A1* | 12/2006 | Wang | G06Q 50/22 378/65 |
| 2007/0217672 | A1* | 9/2007 | Shannon | G06T 7/0006 382/152 |
| 2007/0226258 | A1 | 9/2007 | Lambdin et al. | |
| 2008/0247636 | A1* | 10/2008 | Davis | G06T 19/00 382/152 |
| 2009/0268018 | A1 | 10/2009 | Kasai | |
| 2009/0307628 | A1* | 12/2009 | Metala | G06T 7/0006 715/782 |
| 2011/0066979 | A1 | 3/2011 | Matsui | |
| 2013/0060488 | A1* | 3/2013 | Ghabour | G06T 11/00 702/38 |
| 2014/0184794 | A1* | 7/2014 | Coombs | G01N 27/90 348/143 |
| 2014/0189851 | A1* | 7/2014 | Domke | G06F 21/31 726/17 |
| 2014/0207417 | A1* | 7/2014 | Messinger | G06Q 10/20 702/187 |
| 2014/0207874 | A1* | 7/2014 | Soorianarayanan | H04L 65/403 709/206 |
| 2014/0208159 | A1* | 7/2014 | Soorianarayanan | G06F 11/26 714/27 |
| 2015/0301139 | A1* | 10/2015 | Shames | G01N 24/08 324/309 |

OTHER PUBLICATIONS

U.S. Appl. No. 14/292,680, filed May 30, 2014, Maule.
U.S. Appl. No. 14/292,648, filed May 30, 2014, Bendall.
U.S. Appl. No. 14/292,840, filed May 30, 2014, Jana.
A copy of Invitation to Pay Additional Fees issued in connection with corresponding PCT Application No. PCT/US2015/027050 dated Jul. 29, 2015.

* cited by examiner

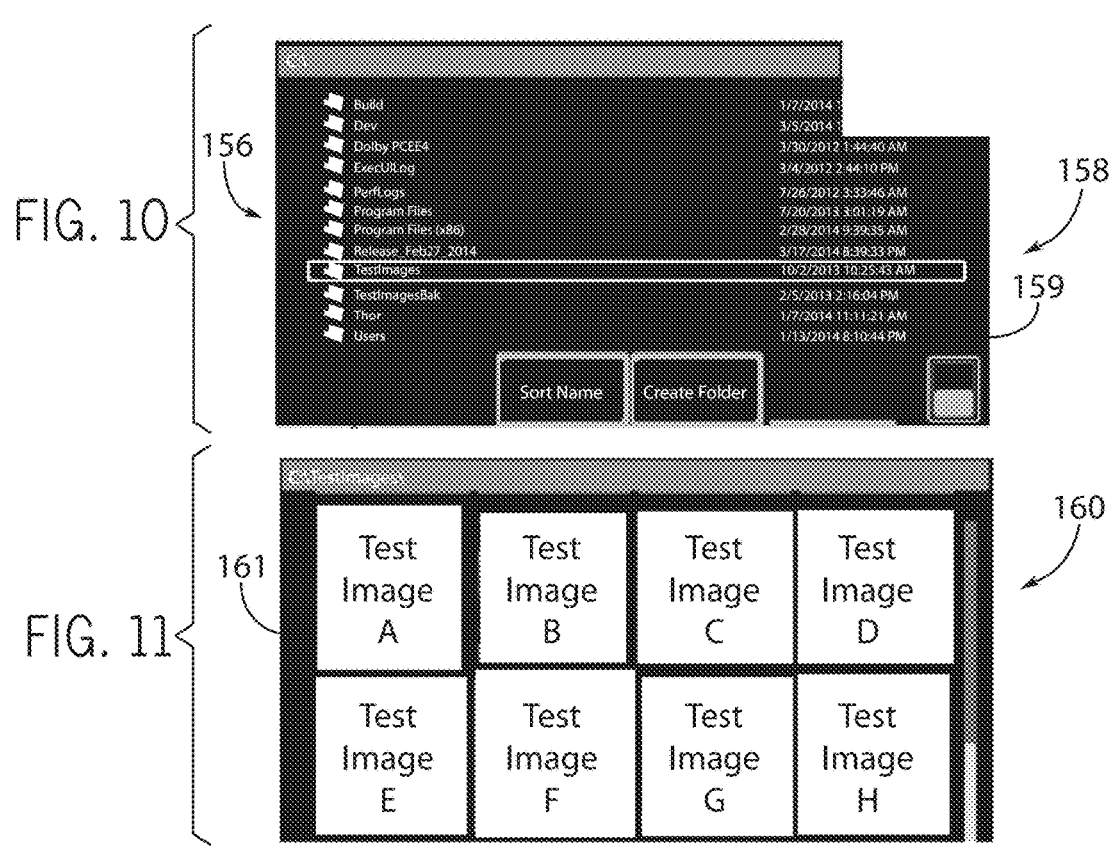

SYSTEMS AND METHODS FOR PROVIDING MONITORING STATE-BASED SELECTABLE BUTTONS TO NON-DESTRUCTIVE TESTING DEVICES

BACKGROUND

The subject matter disclosed herein relates to non-destructive testing devices, and more specifically, to providing state-based selectable buttons to facilitate the use of the non-destructive testing devices.

Certain devices may be used to inspect a variety of systems and facilities, such as power generation equipment and facilities, oil and gas equipment and facilities, aircraft equipment and facilities, manufacturing equipment and facilities, and the like. The inspection equipment may include various non-destructive inspection or non-destructive testing (NDT) devices. For example, video borescopes, portable eddy current inspection devices, portable X-ray inspection devices, and the like, may be used to observe or otherwise inspect the system and facilities using non-destructive inspection techniques. The NDT devices may include user interfaces useful in allowing users to perform various monitoring functions. Unfortunately, such user interfaces may be complex, cumbersome, and time-consuming for users. It may be useful to provide NDT devices with improved user interfaces.

BRIEF DESCRIPTION

Certain embodiments commensurate in scope with the originally claimed invention are summarized below. These embodiments are not intended to limit the scope of the claimed invention, but rather these embodiments are intended only to provide a brief summary of possible forms of the invention. Indeed, the invention may encompass a variety of forms that may be similar to or different from the embodiments set forth below.

In one embodiment, a system includes a portable non-destructive testing (NDT) device. The NDT device includes a processor configured to receive imaging data captured via a sensor of the NDT device, cause a display of the NDT device to display an image to be analyzed based on the imaging data, and cause the display to display a graphical user interface (GUI). The GUI includes a first plurality of user-selectable objects. Each of the first plurality of user-selectable objects is configured to activate one or more monitoring functions of the NDT device. The processor is also configured to cause the display to display at least a first set of the first plurality of user-selectable objects. The first set of the first plurality of user-selectable objects is configured to substantially overlay the image. The first set of the first plurality of user-selectable objects is displayed based at least in part on an inspection state of the NDT device.

In a second embodiment, a non-transitory computer-readable medium having computer executable code stored thereon is presented. The code includes instructions to receive image data captured via a camera of an NDT device, display an image to be analyzed based on the captured image data, and to display a graphical user interface (GUI). The GUI includes a plurality of user-selectable buttons. Each of the plurality of user-selectable buttons is configured to execute one or more monitoring functions of the NDT device. The code also includes instructions to display a first set of the plurality of user-selectable buttons. The first set of the plurality of user-selectable buttons is configured to substantially overlay the image. The first set of the plurality of user-selectable buttons is sequenced based at least in part on a monitoring state of the GUI.

In a third embodiment, a method includes receiving image data captured via a camera of an NDT device, displaying an image to be analyzed based on the captured image data, and displaying a graphical user interface (GUI), wherein the GUI comprises a plurality of graphical touch buttons. Each of the plurality of graphical touch buttons is configured to execute one or more monitoring functions of the NDT device. The method also includes displaying a first set of the plurality of graphical touch buttons. The first set of the plurality of graphical touch buttons is configured to substantially overlay the image. The first set of the plurality of graphical touch buttons is sequenced based at least in part on a monitoring state of the GUI.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 10 is a view of an embodiment of the GUI of FIG. 7 illustrating file folders in a list view in the recall monitoring state, in accordance with the present embodiments;

FIG. 11 is a view of an embodiment of the GUI of FIG. 7 illustrating display thumbnails of images captured during inspection by using the NDT devices, in accordance with the present embodiments;

DETAILED DESCRIPTION

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

Present embodiments relate to a non-destructive testing (NDT) device (e.g., video borescope) useful in presenting and configuring user-selectable buttons (e.g., physical key buttons and/or virtual buttons) as part of a user-configurable GUI. In certain embodiments, the NDT device may provide, for example, one or more default rows of configurable buttons (e.g., physical key buttons and/or virtual buttons) to allow a number functions to be performed by the NDT device. In other embodiments, due to the various applications for which the NDT device may be used, the NDT device may also provide a dynamic arrangement of buttons based on certain states that the NDT device may be in, such as monitoring states (e.g., individual monitoring screen status such as live video state or screen, a freeze-frame state or screen, a recall state or screen, and so forth) of the GUI presented on the display of the NDT device. Furthermore, in certain embodiments, the selectable buttons that appear within each screen of the GUI on the display of the NDT device may be completely user-configurable and stored as part of a user profile or specific NDT device profile. In this way, the user (e.g., operator, technician, engineer, and so forth) may be able to navigate through the NDT device's GUI more comfortably and efficiently, thus facilitating and improving the use and user-friendliness of such devices in various testing and inspection applications.

Figure 1:
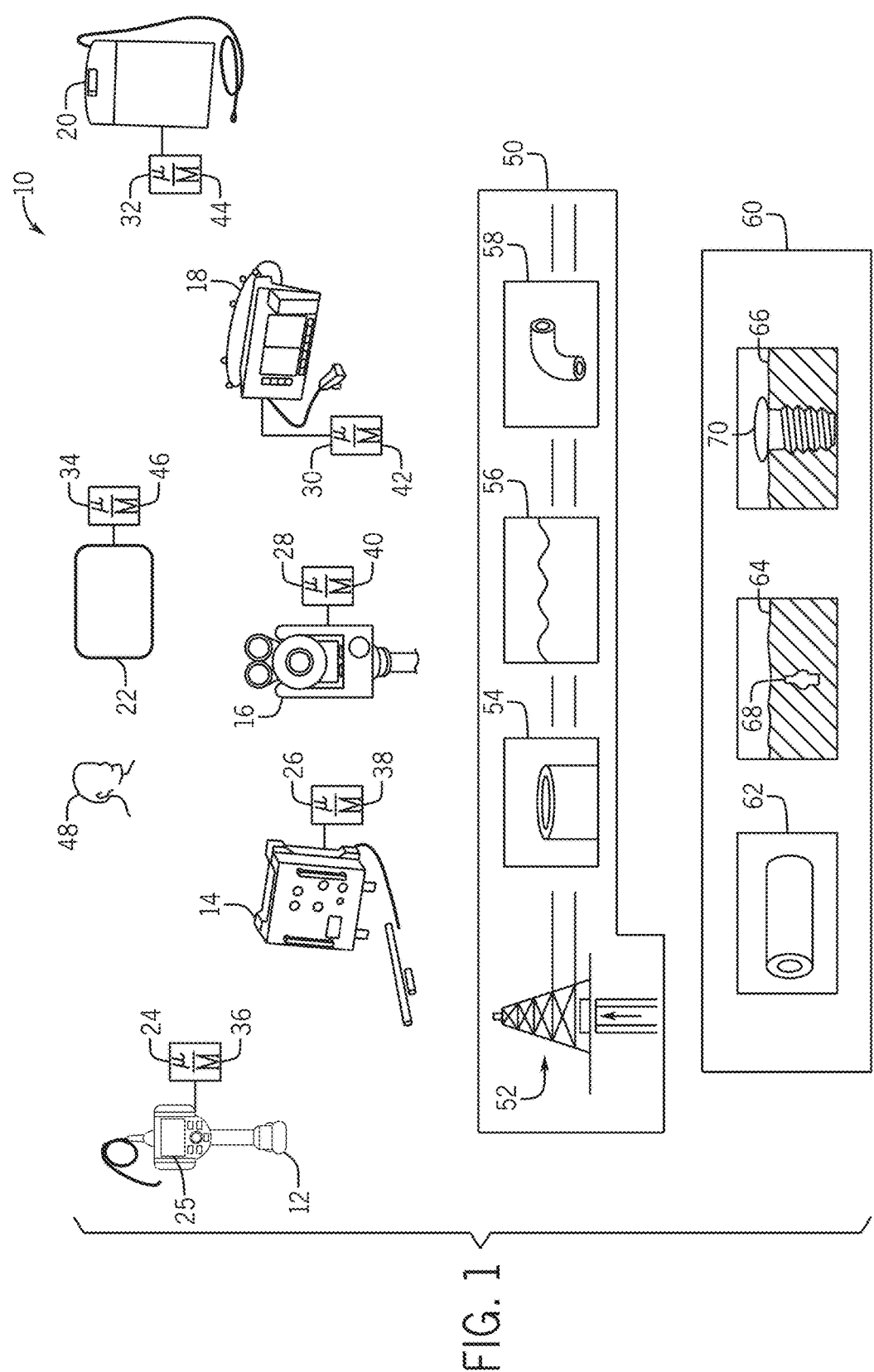
FIG. 1 illustrates embodiments of various non-destructive testing (NDT) devices, in accordance with the present embodiments.

With the foregoing in mind, it may be useful to describe embodiments of various non-destructive testing (NDT) devices, such as example NDT devices 10 as illustrated in FIG. 1. The NDT devices 10 may include any of various portable devices (e.g., mobile electronic devices) that may be useful in monitoring, analyzing, and providing visual inspection, for example, in a gas turbine system, a steam turbine system, a hydraulic turbine system, one or more compressor systems (e.g., aeroderivative compressors, reciprocating compressors, centrifugal compressors, axial compressors, screw compressors, and so forth), one or more electric motor systems, industrial systems including, for example, fans, extruders, blowers, centrifugal pumps, or any of various additional industrial devices or machinery that may be included in an industrial plant or other industrial facility.

In certain embodiments, as depicted in FIG. 1, the NDT devices 10 may include a video borescope 12, an eddy current inspection device 14, a transportable pan-tilt-zoom (PTZ) camera 16, an ultrasonic flaw detector 18, a portable digital radiography device 20, an interface device 22, and so forth. The interface device 22 may include a mobile device (e.g., cell phone, laptop, tablet computer) that may be communicatively coupled to the aforementioned NDT devices 12, 14, 16, 18, 20 suitable for providing enhanced visualization (e.g., at a larger screen display), and for remote control and operations of the NDT devices 12, 14, 16, 18, 20. The NDT devices 12, 14, 16, 18, 20, 22 may be connected to each other and/or to local servers (e.g., local area network [LAN] servers), remote servers (e.g., wide area network [WAN] servers), and "cloud" based devices and services, near-field communication (NFC), and so forth. In one embodiment, the interface device 22 may be a MENTOR™ hardware device or software "app" executable via a mobile device (e.g., cell phone, tablet) available from General Electric Company, of Schenectady, N.Y. Likewise, the 12, 14, 16, 18, 20 devices may also be available from General Electric Company, of Schenectady, N.Y.

The depicted NDT devices 12, 14, 16, 18, 20, and 22 include respective processors 24, 26, 28, 30, 32, 34 and memory 36, 38, 40, 42, 44, and 46. The NDT devices 12, 14, 16, 18, 20, and 22 may additionally include a communications system suitable for communicating with other NDT devices 12, 14, 16, 18, 20, and 22 and with external systems such as "cloud" based systems, servers, computing devices (e.g., tablets, workstations, laptops, notebooks), and the like. The memory devices 36, 38, 40, 42, 44, and 46 may include non-transitory, tangible storage suitable for storing computer code or instructions useful in implementing various techniques described herein and may be executed via the respective processors 24, 26, 28, 30, 32, and 34. As will be further appreciated, the devices 12, 14, 16, 18, 20, and 22 may also include respective displays that may be used to display a graphical user interface (GUI) including user-configurable selectable buttons (e.g., touch buttons) to facilitate use of the devices 12, 14, 16, 18, 20, and 22. For example, the borescope 12, which may be, for example, a video borescope 12, may include a display 25 (e.g., liquid crystal display [LCD], organic light emitting display [OLED], etc.) that may be touch-sensitive (e.g., touch screen) and used to allow a user to interface and/or control the borescope 12 and/or other NDT devices 14, 16, 18, 20, and 22.

In certain embodiments, as previously discussed, a user 48 (e.g., operator, field technician, engineer, and so forth) may utilize the NDT devices 12, 14, 16, 18, 20, 22 to inspect facilities 50, including facilities that may have equipment such as oil and gas equipment 52, and may include locations such as the interior of pipes or conduits 54, underwater (or underfluid) locations 56, and inaccessible or partially inaccessible locations such as locations having curves or bends 58, and so forth. Similarly, Other systems 60 may also be inspected, such as aircraft systems, power generation systems (e.g., gas turbines, steam turbines, wind turbines, hydroturbines, combustion engines, generators, electric motors, and so forth), machinery (compressors, expanders, valves, actuators, and so forth), and the like, that may include conduits 62, various surfaces 64 and 66, and may be used to find undesired cracks 68 or to visualize parts 70, among many other uses.

Figure 2:
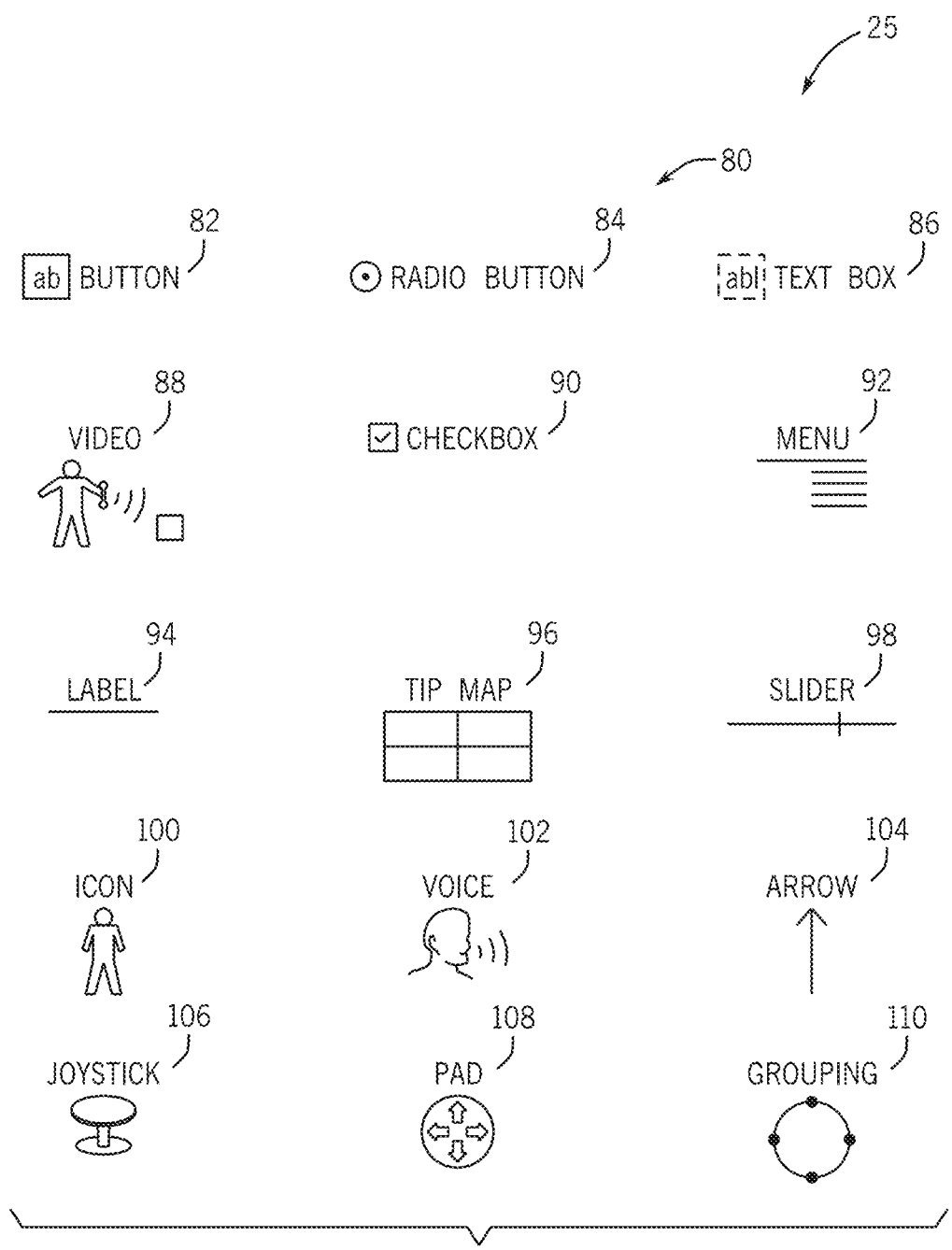
FIG. 2 illustrates embodiments of various objects that may be included as part of a graphical user interface (GUI) of the NDT devices of FIG. 1, in accordance with the present embodiments.

In certain embodiments, as illustrated in FIG. 2, as part of the GUI, the user 48 may be presented with a number of GUI objects 80, including, for example, text objects, multimedia objects, and/or audio objects, suitable for viewing and/or controlling operations of the devices 12, 14, 16, 18, 20, and 22. Specifically, the objects 80 may be provided by the manufacturer of the devices 12, 14, 16, 18, 20, and 22 as part of the GUI and/or other applications useful in operating the devices. For example, as illustrated, the objects 80 may include a selectable button 82 (e.g., graphical selectable button, touch button) that may be used to activate or deactivate components (hardware or software components) of the NDT devices 12, 14, 16, 18, 20, and 22. A labeled radio button 84 may be used to select or deselect components of the NDT devices 12, 14, 16, 18, 20, and 22. A labeled textbox control 86 that may be used to display any number of textual data (e.g., sensor data, annotations, notes, time/date, parameter settings, and so on). A video 88 may be used to display motion images. A labeled checkbox control 90 may be used to check or uncheck features (e.g., hardware or software features) of the NDT devices 12, 14, 16, 18, 20, and 22. A labeled menu control 92 may be used to display hierarchical data. A label display 94 may be used to display a static text and a graphic, as desired. A labeled tip map control 96 may be used to display a current tip position, for example, for the tip of the borescope 12.

Likewise, a labeled slider control 98 may be used to adjust any number of hardware or software components, parameters, and so on by "sliding" to a desired level. An icon 100 may be used to display static images. An audio 102 may be used to provide audio commands, voice annotations, audio instructions, and so on. A labeled arrow control 104 may be used to point to image or video features displayed by the NDT devices 12, 14, 16, 18, 20, and 22. A labeled joystick 106 and/or control pad 108 may be used to manipulate certain components (e.g., tip of the borescope 12) to dispose the components into a desired position. Similarly, a labeled grouping control 110 may be used to "lasso" or group components in order to move the components, delete the components from a screen, and so forth.

However, while FIG. 2 illustrates various objects 80 (e.g., button 82, radio button 84, text box 86, and so forth) that may be displayed via the display 25 (e.g., touch sensitive display) of the borescope 12 and/or other NDT devices 14, 16, 18, 20, and 22, in certain embodiments, it may be useful to provide a specific number of selectable buttons 82 (e.g., virtual key buttons) based on, for example, a select number of monitoring states or screens that the borescope 12 and/or other NDT devices 14, 16, 18, 20, and 22 may be used to present to the user 48. Specifically, in some embodiments, when inspecting devices (e.g., pumps, pipes, conduits, and so forth) and machinery (e.g., gas turbines, steam turbines, wind turbines, hydroturbines, combustion engines, generators, electric motors, compressors, and so forth), there may be a desired group of inspection actions that the user 48 may desire to perform based on state(s) or screen(s) on the borescope 12 (or other NDT device).

Accordingly, in certain embodiments, it may be useful to provide, for example, one or more rows of state-based configurable buttons, thus more efficiently prioritizing desired functionality via the display 25 of the borescope 12 and/or other NDT devices 14, 16, 18, 20, and 22. Moreover, in other embodiments, due to the various applications the borescope 12 and/or other NDT devices 14, 16, 18, 20, and 22 may be used for, the borescope 12 may also provide a different arrangement of buttons at each inspection state or screen presented on the display 25. Indeed, the selectable buttons 82 that appear within each screen of the GUI on the display 25 may be completely user-configurable, manufacturer-configurable, service shop configurable, and stored as a part of a user profile, an NDT device profile, or specific machine profile (e.g., profile for a turbine, compressor, pump, conduit system, and so on).

Figure 3:
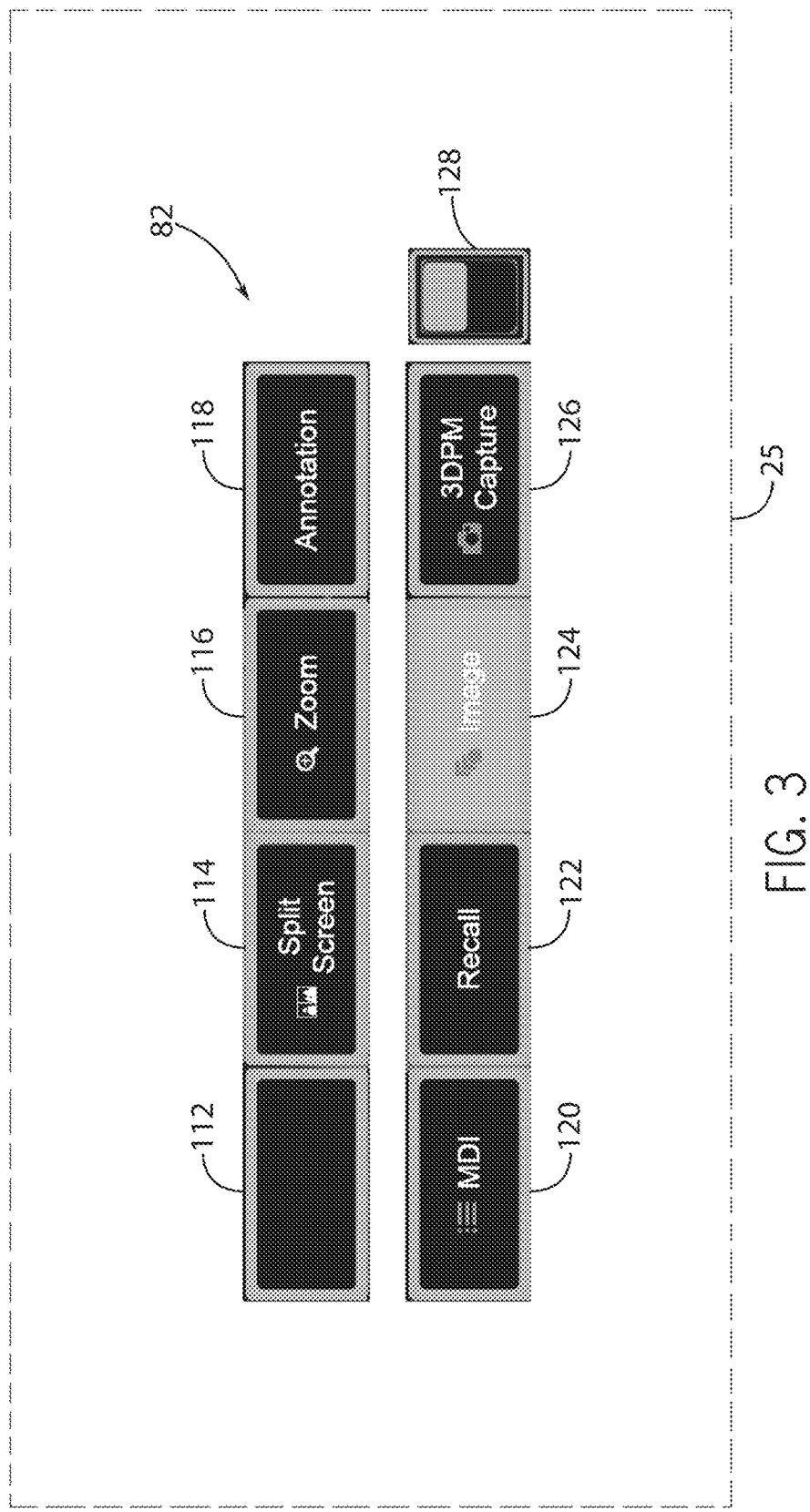
FIG. 3 is an embodiment of a GUI including one or more state-based selectable buttons, in accordance with the present embodiments.

For example, as illustrated in FIG. 3, the selectable buttons 82 may be displayed on the display 25 of the borescope 12 in two rows of 4 selectable buttons 82. The buttons 82 may include virtual buttons actuated via a touch screen, virtual buttons actuated via an input device (e.g., joystick), and/or virtual buttons that are mirrored by physical buttons included in the NDT devices 12, 14, 16, 18, 20, and 22. Indeed, in certain embodiments, the selectable buttons 82 may correspond to, and may be used as user touch alternatives for physical hard buttons (e.g., as illustrated below the display 25 of borescope 12 of FIG. 1) that may be provided on the borescope 12 and/or other NDT devices 14, 16, 18, 20, and 22. Indeed, when selected, the selectable buttons 82 (e.g., virtual buttons 112-126) may trigger various actions based on, for example, the current state or screen of the GUI (e.g., live video, freeze-frame, image recall, etc) of the borescope 12.

Specifically, in one embodiment, each inspection or monitoring state, or screen of the GUI of the borescope 12 may include approximately 8 selectable buttons 82 (e.g., virtual buttons 112-126) per state and separated, for example, into 2 rows. A selectable switch 128 is also provided, suitable for toggling between the upper and lower rows of selectable buttons 82. For example, as further depicted in FIG. 3, the selectable buttons 82 may include a customizable selectable button 112, a split screen selectable button 114 ("Split Screen), a zoom selectable button 116 ("Zoom"), an annotation selectable button 118 ("Annotation"), an Menu Driven Inspection selectable button 120 ("MDI"), a recall selectable button 122 ("Recall"), an image selectable button 124 ("Image"), a 3-dimensional phase measurement capture selectable button 126 ("3DPM Capture"), the selectable switch 128, and so forth. However, it should be appreciated that the position and row of each of the selectable buttons 82 may be user-configurable, and any change a user makes may be stored on the borescope 12 with an associated profile of the user, NDT device, and/or specific machine that the profile is associated with.

In certain embodiments, each of the selectable buttons 82 may correspond to a different function of the borescope 12 and/or other NDT devices 14, 16, 18, 20, and 22. For example, a user selection of the split screen selectable button 114 via the display 25 may launch a split screen (e.g., side-by-side view) that may simultaneously display, for example, a freeze-frame image as well as a live video stream of an area inside or nearby one or more inaccessible portions of monitored devices or machinery. Specifically, a user selection of the split screen selectable button 114 may cause the display 25 of the borescope 12 to display at least two separate side-by-side or top-to-bottom views of, for example, live captured video (e.g., real-time or near real-time images), freeze-frame images (e.g., still images), recall images (e.g., previously captured still images or live video), and so forth. Each displayed image may include an identifier as to whether the image is live image, freeze-frame image, or recall image. Moreover, in this monitoring state (e.g., during inspection), the borescope 12 may allow the user to select via the display 25 which image of the split screen appears as the live image or the freeze-frame image and/or recall image. In some embodiments, as will also be further appreciated, selecting any of the selectable buttons 82 may also cause the display 25 of the borescope 12 to display additional virtual buttons useful in providing additional options to the user.

Similarly, in certain embodiments, a user selection of the zoom selectable button 116 via the display 25 may allow the user to view of magnified view of a monitored device or machinery. Once the zoom selectable button 116 has been selected, the user may further perform one or more touch gestures (e.g., pinch and zoom, double tap, etc.) or other selection technique via the display 25 of the borescope 12 to change or adjust the zoom magnification. Likewise, a user selection of the annotation selectable button 118 via the display 25 of the borescope 12 may allow the user to annotate certain components of the monitored device or machinery to notate that component, for example, for repair, upgrades, and so forth. Annotations may include textual as well as voice annotations.

Continuing, a user selection of the MDI selectable button 120 may launch a Menu Directed Inspection (MDI) application useful in digitally guiding the user through one or more specific inspection processes and/or functions of the borescope 12. For example, the MDI application may guide the user through a specific workflow designed to more efficiently inspect certain components or subsystems of the machinery undergoing inspection. The workflow may include a flow chart-like process with decision point to inspect other components or subsystems based on current inspection results. Additionally, in some embodiments, the user selection of the MDI selectable button 120 may automatically generate a report of the inspection of the monitored device or machinery, as well as automatically organize the results and data acquired via the borescope 12 and/or other NDT devices 14, 16, 18, 20, and 22. Further, in one or more embodiments, the MDI label of the MDI selectable button 120 may change to a label or name of a specific MDI application once the specific MDI application has been selected.

Figure 8:
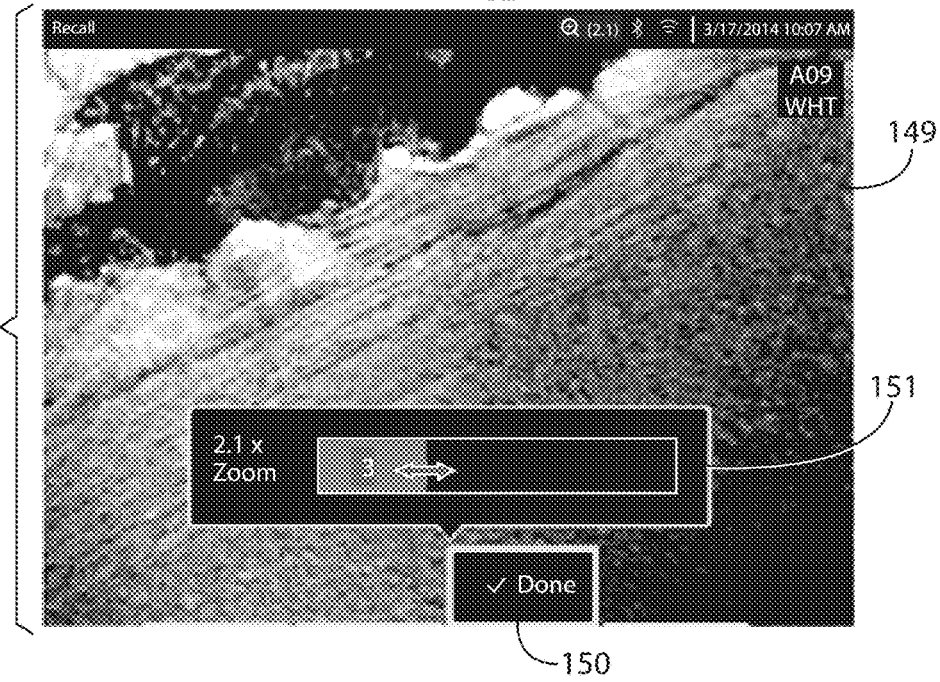
FIG. 8 is a view of an embodiment of the GUI of FIG. 7 illustrating the recall monitoring state including a zoom action, in accordance with the present embodiments.

In a similar manner, a user selection of the recall selectable button 122 via the display 25 may allow the user to view stored files (e.g., stored videos, stored images, stored annotations, stored parameter settings, and so forth) to be displayed, measured, analyzed, further annotated, and so forth. Specifically, as will be further appreciated with respect to FIG. 8, a user selection of the recall selectable button 122 may automatically launch the last saved or last viewed image (e.g., live video image, freeze-frame image) for the user 48 to review. In another embodiment, a user selection of the recall selectable button 122 may automatically launch a list of saved or viewed images from which the user 48 can select therefrom to review. For example, the user 48 may desire to recall (e.g., review a last saved or last viewed image) an image of an annotated outlying combustor within a combustion chamber of a gas turbine. A user selection of the image selectable button 124 via the display 25 may launch an "Image Menu," in which the user may be allowed to alter the appearance a captured and/or viewed image. For example, via a selection of the image selectable button 124 and by way of the launch of the "Image Menu," the user may be allowed to adjust image distortion, image brightness, invert the captured image, adjust image long exposure, contrast, color, as well as perform various adjustments of characteristics of the captured and/or viewed image.

In certain embodiments, a user selection of the three-dimensional phase shifted measurement (3DPM) capture selectable button 126 via the display 25 may allow the user to view three-dimensional surface scanning of internal spaces of the monitored device or machinery. For example, the 3DPM capture selectable button 126 may launch a 3-D phase-shifted image based on, for example, optical phase shifting techniques. This may allow the user 48 to view a 3-D map of one or more inner surfaces of the monitored device or machinery, for example.

In certain embodiments, in addition to the selectable buttons 82 that may appear on the display 25 of the borescope 12, the GUI of the borescope 12 display 25 may also include the selectable switch 128. Specifically, the selectable switch 128 may be selected (e.g., via a single tap, double tap, flick, drag, scroll, long-press touch gesture on the display 25, joystick) to toggle between displaying and hiding the upper and lower rows selectable buttons 82. In other embodiments, the selectable switch 128 may be a menu key, and thus a user touch gesture or selection to switch the selectable switch 128 may allow the user to toggle between one or more menu windows (e.g., menu pop-up windows) or status bars that may be associated with each of the selectable buttons 82. For example, a user double tap gesture of the selectable switch 128 may hide or display the selectable buttons 82, menu windows, and/or status bar, while, for example, a single tap gesture of the selectable switch 128 may cause the display 25 of the borescope 12 to switch between displaying or hiding the upper and lower rows of the selectable buttons 82.

Figure 4:
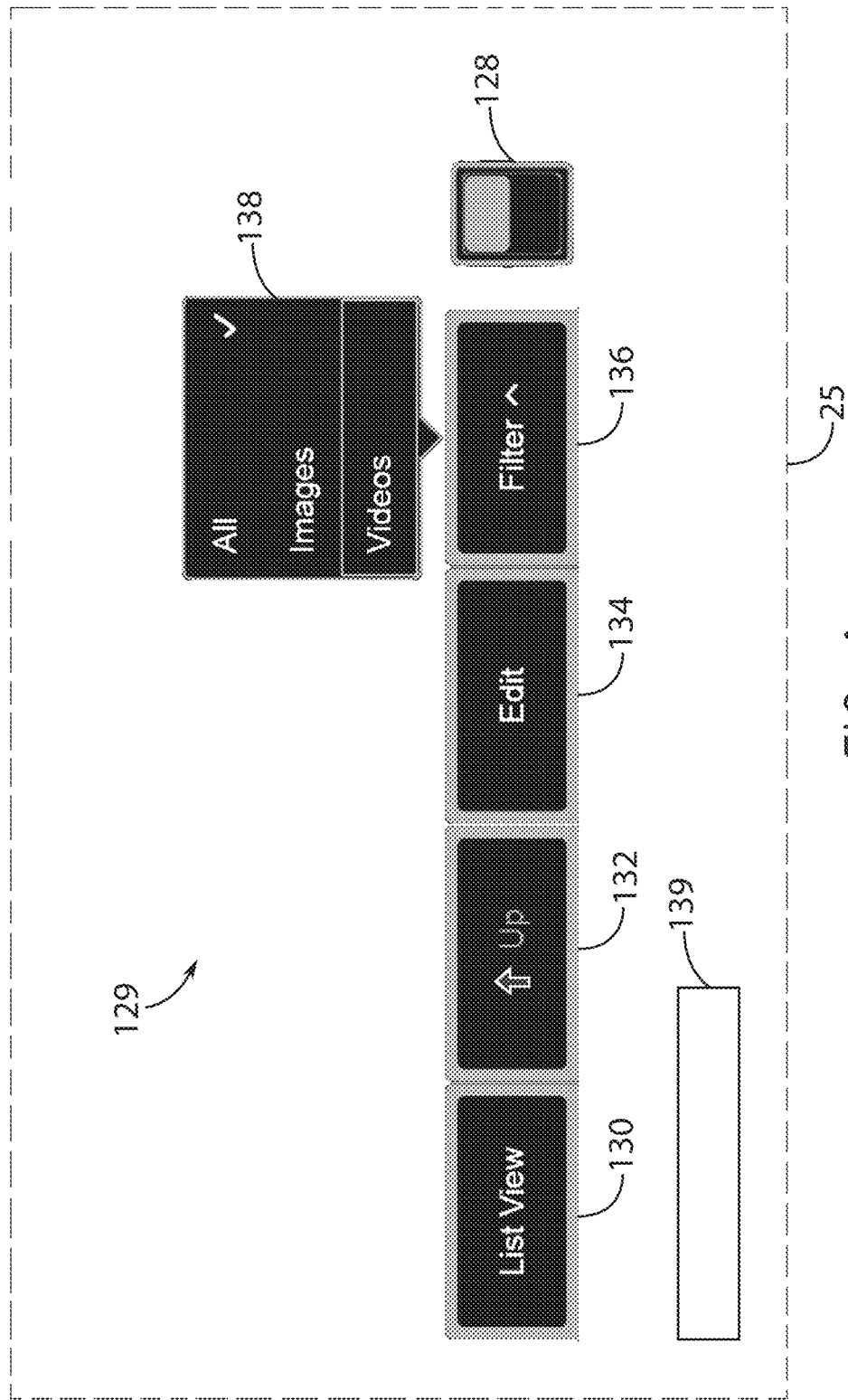
FIG. 4 an embodiment of the GUI of FIG. 3 including additional graphical selectable buttons and a pop-up menu, in accordance with the present embodiments.

As previously discussed, the buttons 82 may each be representative of a different state or screen, and may be used to navigate between states or screens. For example, as illustrated by FIG. 4, and as will be further discussed with respect to FIG. 8, a number of additional selectable buttons 129 (e.g., 130-136) may appear in response to a user selection of one or more of the selectable buttons 82. Specifically, the additional selectable buttons 129 (e.g., selectable buttons 130-136) as depicted in FIG. 4 may include selectable buttons 129 that may appear in response to a user selection of the recall selectable button 122 (shown in FIG. 3) or other selectable button 82 that may include additional control options. By way of example, upon a user selection of the recall selectable button 122 via the display 25 of the borescope 12, the display 25 may display a list view selectable button 130 ("List View"), an up selectable button 132 ("Up"), an edit selectable button 134 ("Edit"), and a filter selectable button 136 ("Filter"). As depicted, the list view button 130, the up button 132, the edit button 134, and filter button 136 may appear to allow the user of the borescope 12 to view, edit, and display stored live video images, freeze-frame images, stored parameter settings, and so forth.

Similarly, a menu popup list 138 may appear in response to a user selection of one or more of the selectable buttons 82, 129 (e.g. filter selectable button 136). It is to be understood that any button 82 may include a visual representation, such as an icon, color, text, and so on, for example, the caret character "^" shown next to the word "Filter" in button 136, that may tell the user that a long press or other button action may show a popup list. It should also be understood that other popup lists may include any of the objects 80 depicted in FIG. 2. It should also be appreciated that the additional selectable buttons 129 (e.g., appearing in response to a user selection of the recall button 122) as depicted in FIG. 4 are included merely for the purpose of illustration. Indeed, in other embodiments, the additional selectable buttons 129 may also include selectable buttons allowing the user to select to play audio ("Stereo"), record audio or video ("Record"), invoke a help option ("Help") to facilitate inspection, bring forth a list of stored profiles, create a profile, transmit a profile, perform one or more measurements, perform comparisons ("Comparison") and so forth, that may appear in response to a user selection of the respective selectable buttons 82. Indeed, the buttons 82 may include any of the functions available in the NDT devices 12, 14, 16, 18, 20, and 22 including the functions provided via the objects 80. Also depicted is a minimized button 139. The minimized button 139 may be displayed either as a button placeholder when a row is displaying less than the total number of buttons (e.g., four per row in the depicted example). Indeed, some states may use less than the total number of buttons (e.g., less than four), so the button 139 may be used as placeholder.

Figure 5:
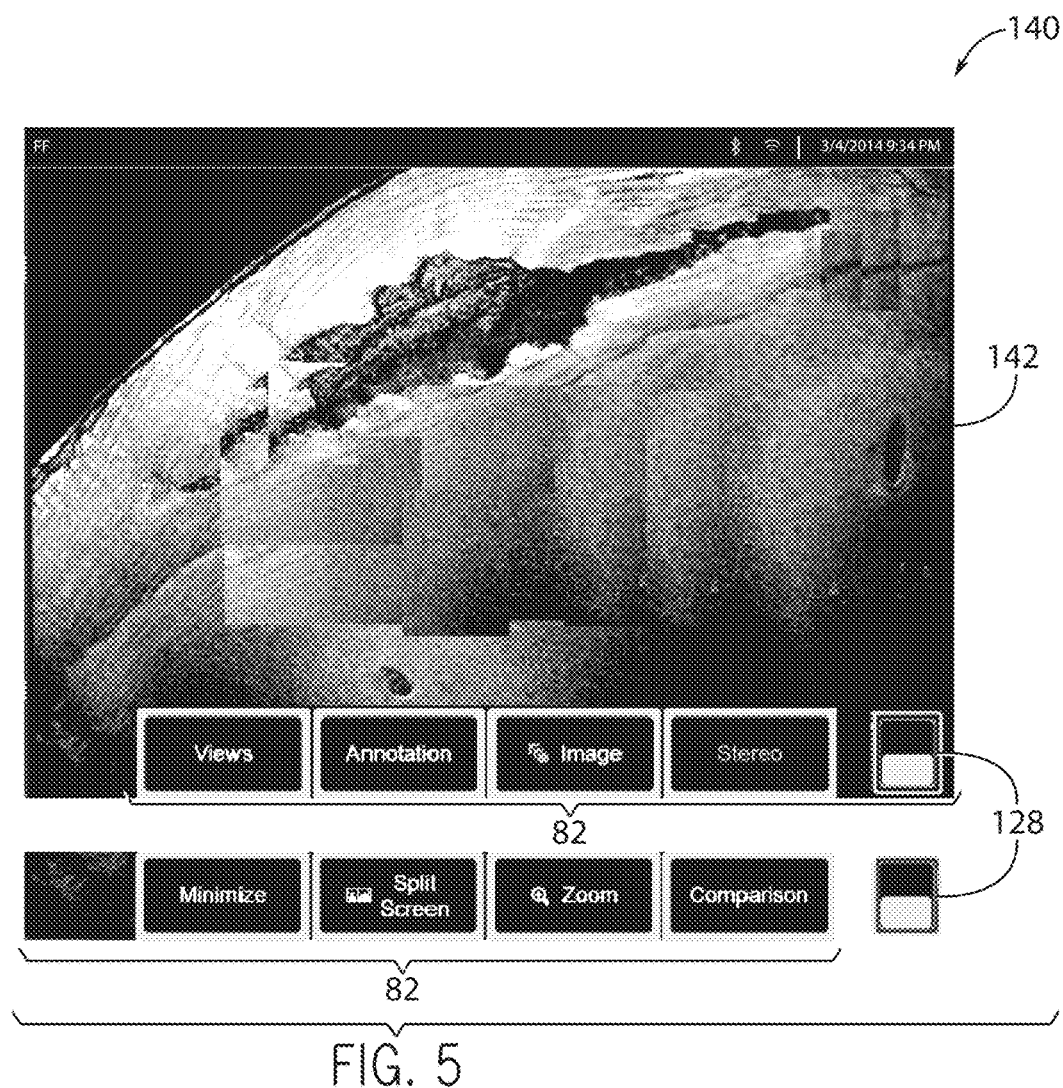
FIG. 5 is a view of an embodiment of the GUI of FIG. 3 illustrating a freeze-frame monitoring state, in accordance with the present embodiments.

Turning now to FIGS. 5-12, which respectively illustrate various states or screens and the corresponding selectable buttons 82 that may be presented on the display 25 of the borescope 12 and/or other NDT devices 14, 16, 18, 20, and 22 based on the current inspection state of the system (e.g., live video monitoring, freeze-frame image monitoring, image recall, and so forth) as discussed above with respect to FIGS. 3 and 4. For example, FIG. 5 illustrates a freeze-frame ("FF") monitoring state or screen 140, which includes a captured image. As depicted, the freeze-frame ("FF") monitoring state or screen 140 may include a freeze-frame image 142 (e.g., captured still image) of a portion of a monitored device or machinery. As illustrated, in the freeze-frame ("FF") monitoring state or screen 140, the upper row of selectable buttons 82 may include the annotation selectable button 118 ("Annotation"), the image selectable button 124 ("Image"), as well as additional selectable buttons 82 ("Views") and ("Stereo"). Similarly, a user selection of the selectable switch 128 may cause the display 25 to display the lower row of selectable buttons 82 instead of or in addition to the upper row, which may include the zoom selectable button 116 ("Zoom"), the split screen selectable button ("Split Screen") 114, as well as additional selectable buttons 82 ("Minimize") and ("Comparison").

As previously discussed above with respect to FIGS. 3 and 4, each of the selectable buttons 82 displayed in the respective monitoring states or screens may be, in some embodiments, completely user-configurable. For example, referring again to FIG. 5, the user may reorder the selectable buttons 82 that appear within the upper row of selectable buttons 82, reorder the selectable buttons 82 that appear within the lower row of selectable buttons 82, switch the selectable buttons 82 between the upper and lower rows of the selectable buttons 82, modify the possible selection of selectable buttons 82 (e.g., any possible combination of selectable buttons 82 up to approximately 8 selectable buttons 82) that appear in the freeze-frame ("FF") monitoring state or screen 140, and so forth. The GUI may also include additional hidden rows or columns of selectable buttons 82 from which the user 48 may choose from. Specifically, the user 48 may configure each of the selectable buttons 82 according to the user's preference and/or the specific application. In this way, by providing the borescope 12 and/or other NDT devices 14, 16, 18, 20, and 22 with a monitoring state-based or user-configurable GUI, the user 48 (e.g., operator, technician, engineer, and so forth) may be able to navigate through the GUI more comfortably and efficiently, thus facilitating and improving the use and user-friendliness of such devices in various monitoring applications.

Figure 6:
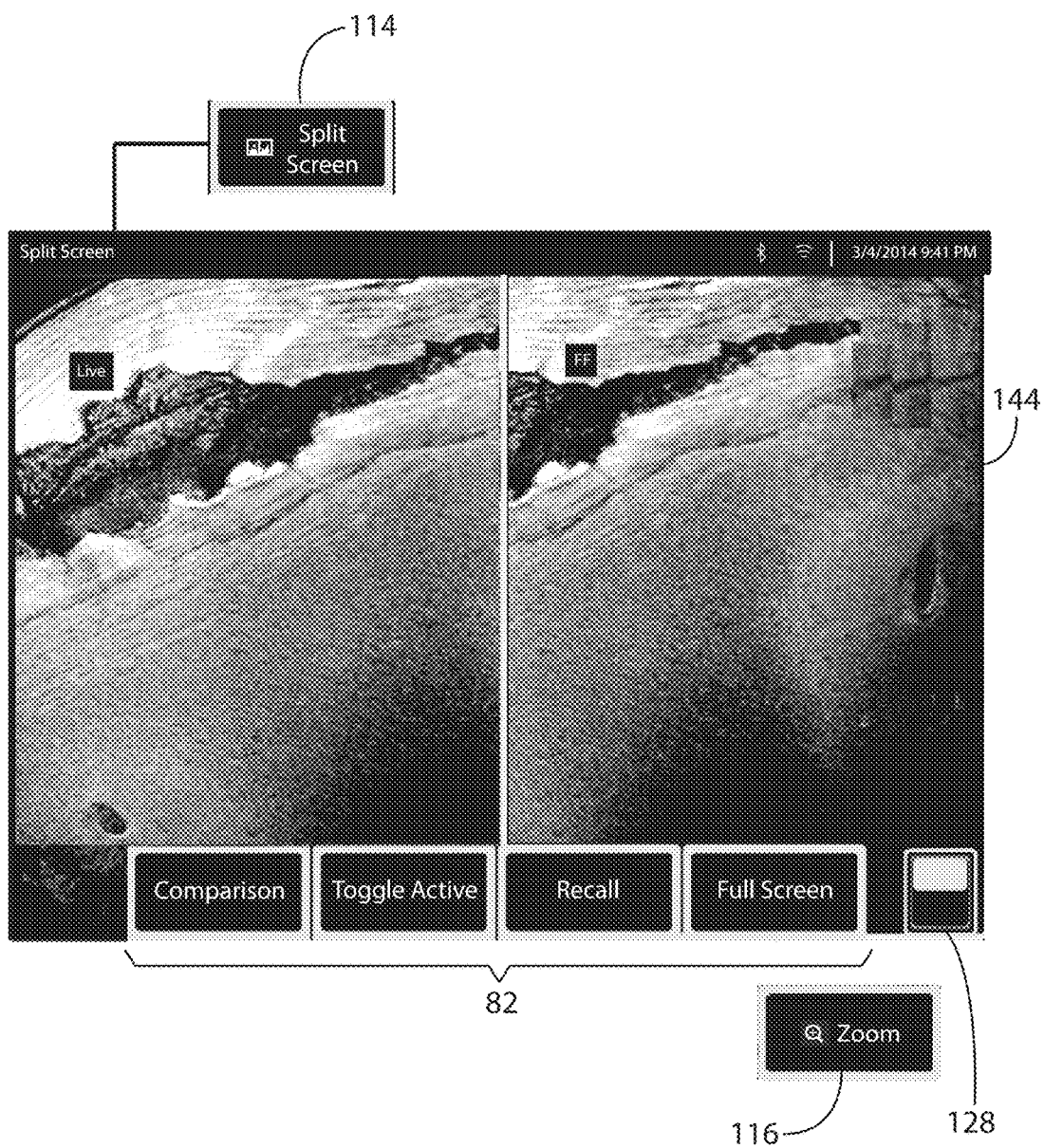
FIG. 6 is a view of an embodiment of the GUI of FIG. 3 illustrating a split-screen view of a live video monitoring state and a freeze-frame monitoring state, in accordance with the present embodiments.

In certain embodiments, as partially illustrated in FIG. 5, but as will be further discussed with respect to FIG. 6, the techniques described herein may enable the user 48 to switch between freeze-frame ("FF") monitoring state or screen to a live video ("Live") monitoring state or screen, or to display both of these states or screens simultaneously via a split screen 144. For example, as illustrated in FIG. 6, a user selection of the split screen selectable button 114 may launch the split screen 144, which includes a live video ("Live") monitoring state of the monitored device or machinery and a freeze-frame ("FF") monitoring state of the monitored device or machinery appearing in a side-by-side presentation. Specifically, the user 48 may be presented with a live video (e.g., real-time video) of the monitored device or machinery while simultaneously presented with a freeze-frame image (e.g., still image) of the monitored device or machinery to, for example, facilitate the analysis performed by the user 48. As further depicted, the selectable buttons 82 (e.g., "Comparison," "Toggle Active," "Recall," and "Full Screen") may appear across the freeze-frame ("FF") screen and the live video ("Live") screen.

Figure 7:
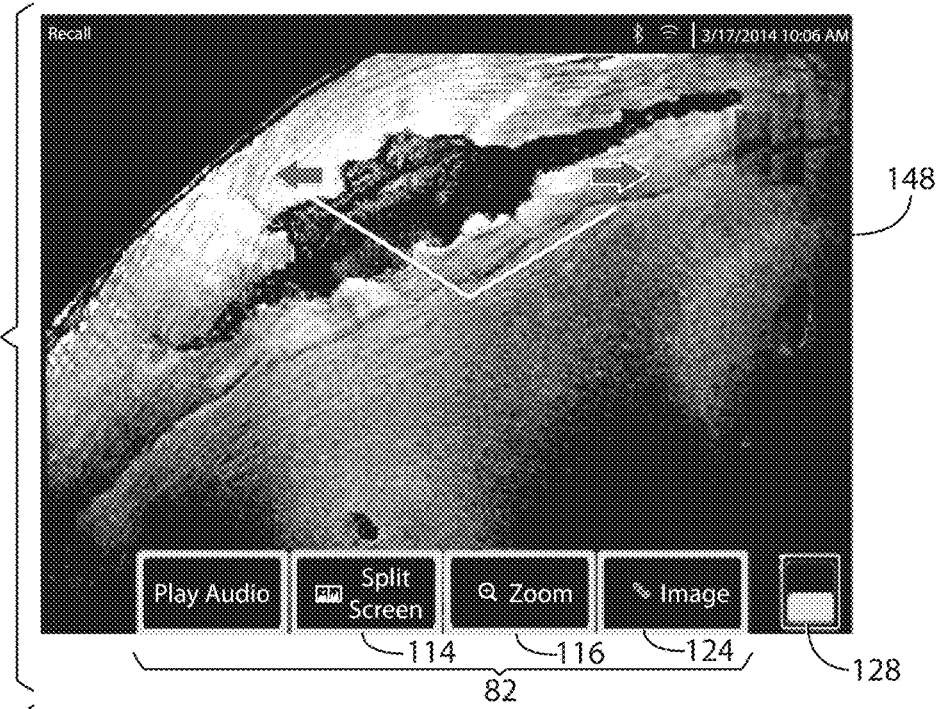
FIG. 7 is a view of an embodiment of the GUI of FIG. 3 illustrating a recall monitoring state, in accordance with the present embodiments.

In a similar manner, FIG. 7 illustrates the recall ("Recall") monitoring state or screen 148. As previously noted and as illustrated in FIG. 7, a user selection of the recall selectable button 122 via the display 25 may allow the user to view stored files (e.g., stored video, stored images, stored annotations, stored parameter settings, and so forth) to be displayed, measured, annotated, further analyzed, and so forth. For example, the recall monitoring state or screen 148 depicts an area of interest of an otherwise inaccessible portion of the monitored device or machinery, and also the selectable buttons 82 (e.g., "Play Audio," "Split Screen," "Zoom," and "Image") and the selectable switch 128. FIG. 7 further depicts that one or more of the selectable buttons 82 may be selected in the recall monitoring state.

For example, while analyzing a recalled image via the recall screen 148, the user 48 may desire to analyze a magnified view of the displayed area of interest of the monitored device or machinery. Thus, the zoom selectable button 116 ("Zoom") may provided as one of the number (e.g., 4, 8, etc.) of the selectable buttons 82 available to be selected by the user 48 in the recall state. A user selection of the zoom selectable button 116 may launch a magnified view of the recalled image of the area of interest of the monitored device or machinery as illustrated by screen 149 in FIG. 8. The screen 149 of FIG. 8 may also include a zoom bar 151, enabling the user 48, for example, to easily adjust (e.g., by performing one or more touch gestures via the display 25) the magnification of the recalled image. A done button 150 ("Done") may also be provided to save the recalled image at the adjusted magnification.

Figure 9:
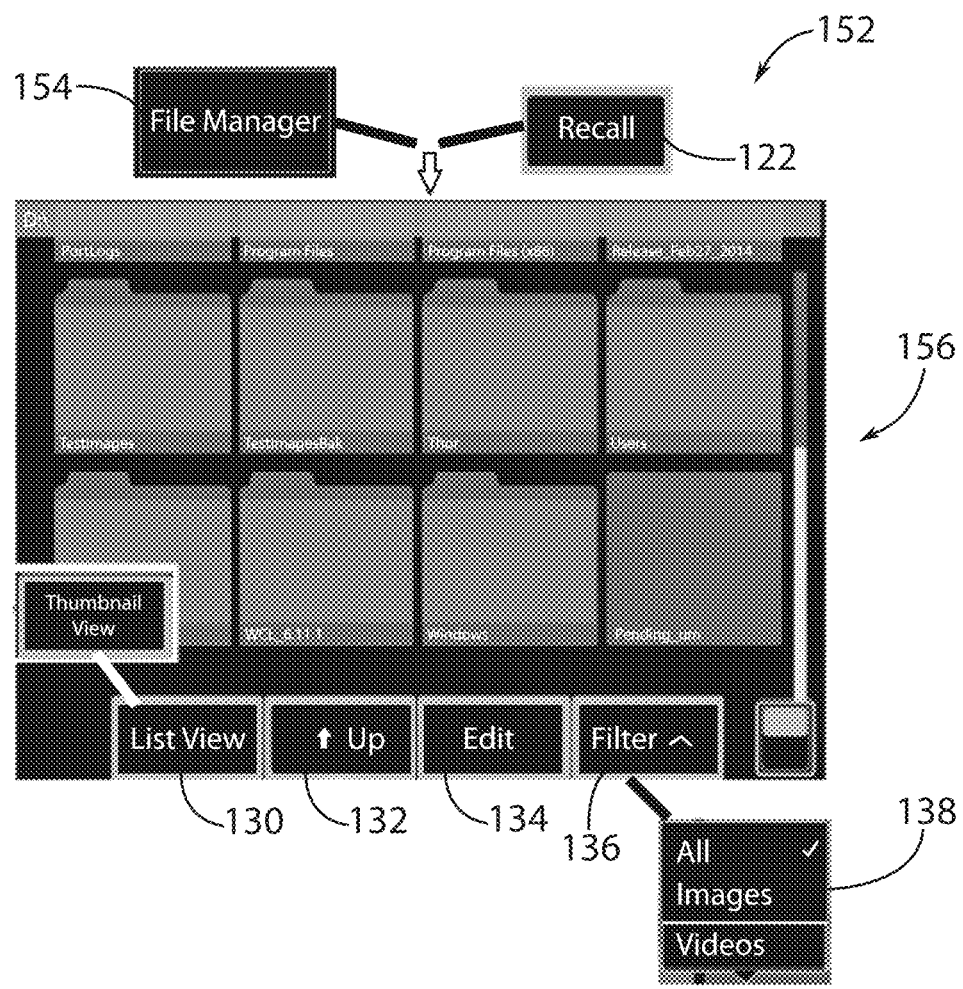
FIG. 9 is a view of an embodiment of the GUI of FIG. 7 illustrating thumbnail views of recall files in the recall monitoring state, in accordance with the present embodiments.

Turning now to FIG. 9, in certain embodiments, as part of the recall monitoring state or screen 148, a file manager selectable button 154 ("File Manager") may be displayed via the display 25 for selection to view one or more of the files stored on the borescope 12 and/or other NDT devices 14, 16, 18, 20, and 22. For example, FIG. 9 illustrates a screen 152, which depicts a number of file folders 156 available for recall viewing, shown as folder icons. As illustrated, the user 48 may be allowed to manage (e.g., filter) the stored files (e.g., images, videos, stored settings, and so forth). As a further example, screen 158 of FIG. 10 depicts the file folders 156 in a list view. Details 159 corresponding to each folder, such as date of creation, time, and size, and so on, may also be displayed by screen 158. Once a folder is navigated into, screen 160 may display thumbnails 161 of images captured during inspection by using the NDT devices 12, 14, 16, 18, 20 and 22, as shown in FIG. 11. The thumbnails may be moved onto a different NDT device 12, 14, 16, 18, 20 and 22 and/or external devices, including cloud-based systems, via wireless systems, wired systems, storage cards (e.g., USB cards, SD cards), and the like.

Figure 12:
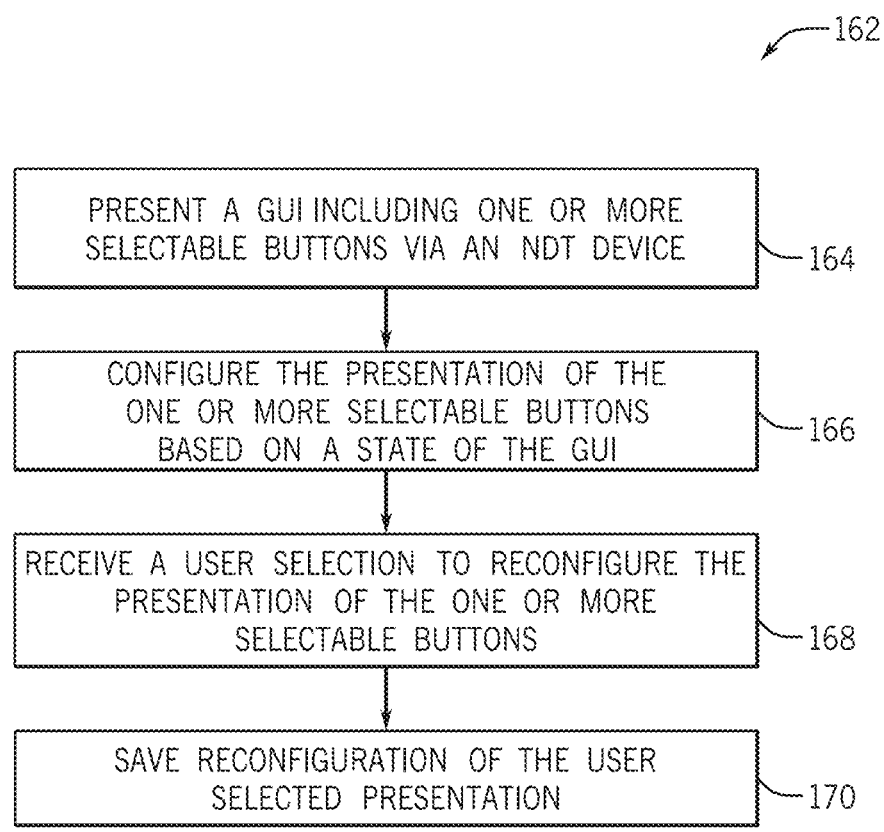
FIG. 12 is a flowchart illustrating an embodiment of a process useful in presenting and configuring selectable buttons (e.g., touch buttons) as part of a GUI to reduce complexity and facilitate the use of NDT devices.

Turning now to FIG. 12, a flow diagram is presented, illustrating an embodiment of a process 162 useful in presenting and configuring selectable buttons 82 as part of a GUI using, for example, one or more of the NDT devices (e.g., borescope 12) depicted in FIG. 1. The process 162 may include code or instructions stored in a non-transitory computer-readable medium (e.g., the memory devices 36, 38, 40, 42, 44, and 46) and executed, for example, by the respective processors 24, 26, 28, 30, 32, 34 included in the various NDT devices 12, 14, 16, 18, 20, and 22. The process 162 may begin with the processor 24 of the borescope 12 presenting (block 164) a GUI including one or more a selectable buttons via a display of an NDT device (e.g., borescope 12). For example, the selectable buttons 82 may be displayed on the display 25 of the borescope 12 in approximately 2 rows of 4 selectable buttons 82, which may include, for example, the split screen selectable button 114 ("Split Screen"), the zoom selectable button 116 ("Zoom"), the annotation selectable button 118 ("Annotation"), the MDI selectable button 120 ("MDI"), the recall selectable button 122 ("Recall"), the image selectable button 124 ("Image"), and the 3DPM capture selectable button 126.

The process 162 may then continue with the processor 24 of the borescope 12 configuring (block 166) the presentation of one or more of the one or more selectable buttons based on an inspection (e.g., monitoring) state of the GUI presented on the display 25 of the borescope 12 (e.g., video borescope). For example, the processor 24 of the borescope 12 may configure or arrange the presentation the selectable buttons 82 based on, for example, whether the GUI is currently in either the live video ("Live") monitoring state, the freeze-frame ("FF") monitoring state, the recall ("Recall") monitoring state, and so forth. Specifically, the borescope may default to displaying the selectable buttons 82 according to the expected functions to be performed by the user corresponding to one of the respective monitoring states (e.g., live, freeze-frame, recall, and so forth). The process 162 may then continue with the processor 24 of the borescope 12 receiving (block 168) one or more user selections to reconfigure the presentation of the selection of soft key buttons. For example, the processor 24 of the borescope 12 may receive a user indication to arrange and/or reorder (e.g., arrange the order in which the selectable buttons 112-124 appear or rearrange the combination of selectable buttons 112-124) the presentation of the selectable buttons 82 based on, for example, user preference, user application, reliability, ease-of-use, and so forth.

The borescope 12 may further allow the user to arrange and/or reconfigure the location on the display 25 the selectable buttons 82 appear based on the monitoring state, as well as reconfigure the possible control options that each selectable button 82 includes as an extension upon selection. For example, as previously discussed with respect to FIGS. 7 and 8, in the recall monitoring state, the processor 24 of the borescope 12 may present additional selectable buttons 82 such as a file manager selectable button 154 in response to the user selecting the recall selectable button 122 ("Recall"). In this way, by providing the borescope 12 and/or other NDT devices 14, 16, 18, 20, and 22 with a monitoring state-based or user-configurable GUI, the user 48 (e.g., operator, technician, engineer, and so forth) may be able to navigate through the GUI more comfortably and efficiently, thus facilitating and improving the use and user-friendliness of such devices in various monitoring applications.

The process 162 may then conclude with the processor 24 of the borescope 12 saving (block 170) and/or storing the user-configurable settings or presentation of the selectable buttons 82 for future use. For example, in one embodiment, as will be further appreciated, the processor 24 of the borescope 12 may generate one or more profiles associated with the user 48 or, in other embodiments, associated with the particular device or machinery of which the borescope 12 is monitoring.

Figure 13:
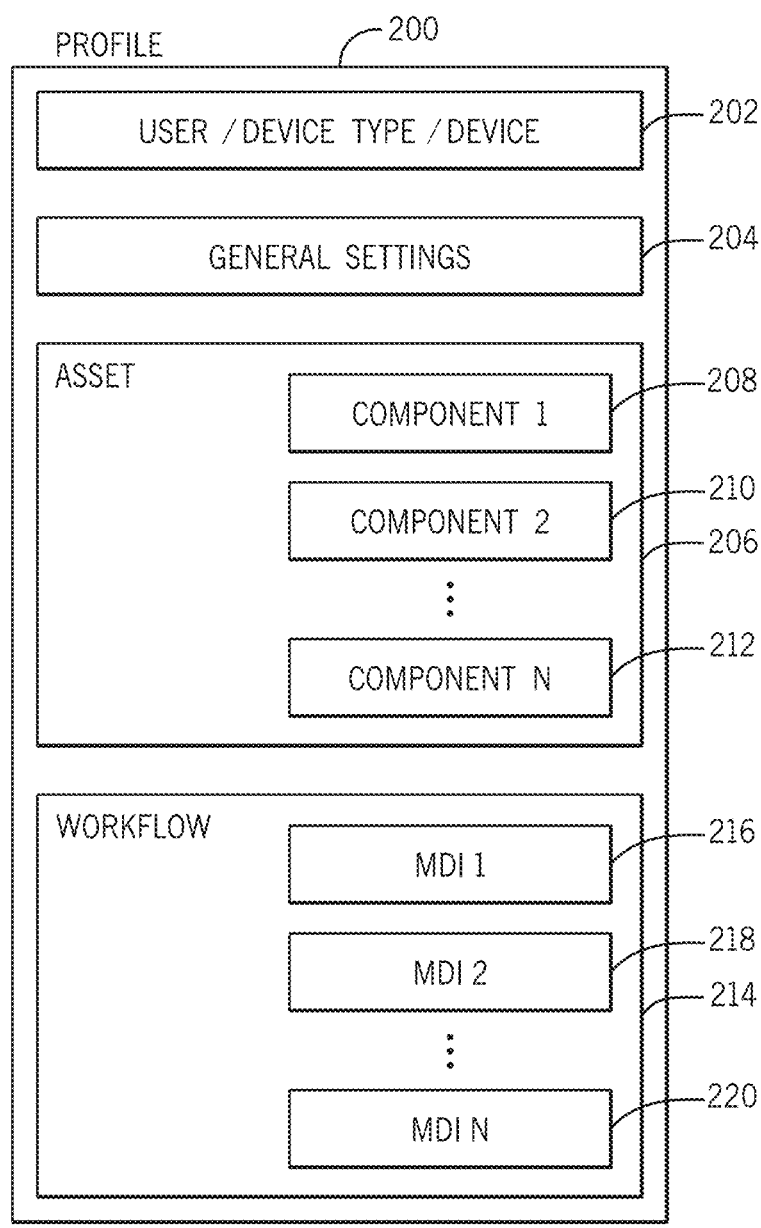
FIG. 13 is an embodiment of a profile suitable for customizing the NDT devices to enable a more efficient interaction between the NDT devices and a user, in accordance with the present embodiments.

Turning now to FIG. 13, the figure is an embodiment of a profile 200 suitable for customizing the NDT devices 12, 14, 16, 18, 20, 22 to enable a more efficient interaction between the NDT devices 12, 14, 16, 18, 20, 22 and the user 48. The profile 200 may be stored in the memories 36, 38, 40, 42, 44, and 46 as data and/or computer instructions and may be executed by processors 24, 26, 28, 30, 32, 34. The profile 200 may be stored in a variety of formats, textual and/or binary, including XML, XAML, INI, and so on. In the depicted embodiment, the profile 200 includes an identification section 202. The identification section 202 may be used to uniquely identify the profile 200 and to associate the profile 200 with a variety of entities. For example, the profile 200 may be associated with a user (e.g., a user profile), with a user group (e.g., a group-based profile), with a device type (e.g., a type of borescope or any other NDT devices 12, 14, 16, 18, 20, 22), with a particular device, such as a specific borescope 12 or 14, 16, 18, 20, 22 (e.g., NDT device identified by device serial number), with a machine type (e.g., machine-based profile such as a gas turbine based profile), with a particular machine (e.g., identified by serial number, such as a specific gas turbine), or a combination thereof.

Accordingly, the profile 200 may be loaded based on which user 48 is using the NDT device 12, 14, 16, 18, 20, 22, which group the user 48 belongs to, what type of NDT device 12, 14, 16, 18, 20, 22 is being used, which specific NDT device 12, 14, 16, 18, 20, 22 is being used, what type of machinery is being inspected, what specific machine is being inspected, the geographic location of the inspection site, or combination thereof.

The profile 200 may include a general settings section 204 useful for storing information related to one or more subsettings. The one or more subsettings may include system settings, screen and display settings, connectivity settings, image and video settings, and/or measurement and annotation settings. The system settings may store parameters such as preferred language to use, power management mode to use (e.g., conservation of power mode), whether or not to use a watermark logo (e.g., logo to insert into images/videos), a preferred time format, a preferred date format, USB settings (e.g., USB slave mode used to upload/download files when the NDT device is connected to an external computing system), and a steering sensitivity. The steering sensitivity may include parameters related to how much to move a tip probe, for example, based on user input.

The screen and display settings may include all parameters that may be associated with the NDT device 12, 14, 16, 18, 20, 22 screen and/or GUI display, such as whether or not touchscreen input is enabled, whether or not to display a tip map (e.g., visual display showing a tip position in one of four quadrants), whether or not to display a logo, such as a manufacturer's logo, an LCD brightness to use, whether or not to display certain items, such as a mute icon, a date, a time, and so on. The connectivity settings may include parameters such as whether or not to enable wireless or wired connectivity, and settings used to connect, such as network names, associated passwords, packet sizes, frequencies to use, and so on. A variety of wireless and wired connectivity may be supported, including IEEE 802.11x (e.g., IEEE 802.11a, b, c, g, n, and so on), Bluetooth, Zigbee, mesh networks, personal area networks, local area networks, and wide area networks. The connectivity settings may additionally include network drives to connect to, and folders of the NDT devices 12, 14, 16, 18, 20, 22 to share.

The image and video settings may include parameters such as preferred file formats to store images and video (e.g., JPEG, BMP, PNG, TIFF, AVI, MPEG4, H.264 high, H.264 low), locations to store images and video (e.g., preferred storage folders), whether or not a microphone is enabled by default, which microphone to use (e.g., internal microphone, external microphone such as a Bluetooth microphone), which speaker to use (e.g., internal speaker, external speaker such as a Bluetooth speaker), certain settings associated with menu directed inspections (e.g., whether to save an inspection stage name when saving images or video), and distortion correction tables useful to more clearly display tip images.

The measurement and annotation settings may include parameters such as parameters useful in managing or calibrating inspection tips (e.g., 3DPM tips, stereoscopic inspection tips), whether or not a zoom window (useful in cursor placement during measurement) is enabled or disabled, parameters useful in saving or loading preset data, such as inspection notes or annotation data, units of measurements to use, and so on.

The profile 200 may additionally include support for assets or machinery in section 206. For example, the profile 200 may store all parameters previously described with respect to section 204 in section 206 to use the previously mentioned parameters with an asset type or a specific asset identifiable, for example, via a serial number or any other unique identification that may also be stored in section 206. Accordingly, during inspection, the section 206 may load parameters into respective memories 36, 38, 40, 42, 44, and 46 of the NDT devices 12, 14, 16, 18, 20, and 22 to be applied when inspecting the asset identified via section 206. Likewise, the profile 200 may include support for a subsystem or component of the asset via sections 208, 210, 212 in the same manner. That is, sections 208, 210, 212 may store all parameters as described above with respect to sections 204, 206 but for a component or subsystem type (e.g., compressor system of a turbine system), or specific subsystem or component. In this manner, the profile 200 may enable a more customized inspection of a variety of assets or machinery 50, 60.

A variety of workflows may also be supported in section 214. A workflow may include a process or processes useful in inspection assets or machinery 50, 60 by providing for a guided inspection of the assets or machinery 50, 60. For example, the workflow 214 may include one or more menu driven inspection (MDI) sections 216, 218, 220. Each MDI section 216, 218, 220 may include all of the parameters mentioned above with respect to sections 204, 206, 208, 210, 212 but directed at specific MDIs. For example, when executing an MDI directed at performing a hot gas path inspection (HGPI) of the gas turbine, an MDI corresponding to the HPGI process, such as the MDI 216 may be used to retrieve and load parameters into respective memories 36, 38, 40, 42, 44, and 46 of the NDT devices 12, 14, 16, 18, 20, and 22 to be applied when performing the HGPI process. Accordingly, the NDT devices 12, 14, 16, 18, 20, 22 may be set with a specific set of parameters, including system settings, screen and display settings, connectivity settings, image and video settings, and/or measurement and annotation settings. In this manner, any number of workflows or processes used to test, inspect, or more generally observe the facilities and machinery 50, 60, may be more efficiently performed. It should also be noted that multiple profiles 200, each profile 200 having multiple sections 202-220, may be used. The profile 200 may also store a user created configuration of the buttons displayed with respect to the figures above (e.g., FIGS. 5-12). That is, once the user 48 has defined a preferred virtual button layout and display, the layout and display may then be stored in the profile 200.

Figure 14:
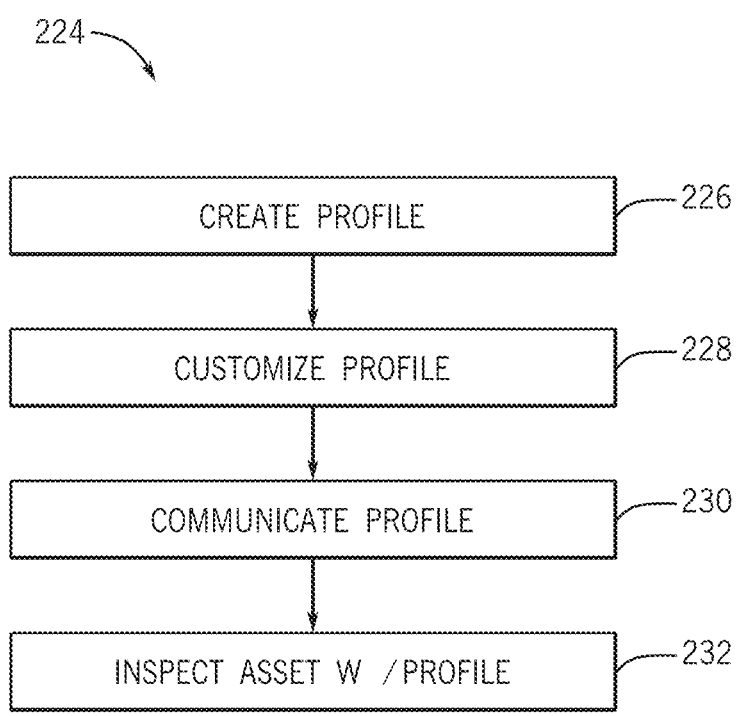
FIG. 14 is a flowchart of an embodiment of a process suitable for creating, executing, and disseminating the profile shown in FIG. 13, in accordance with the present embodiments.

FIG. 14 is a flowchart of an embodiment of a process 224 suitable for creating, executing, and disseminating the profile 200 shown in FIG. 13. The process 224 may include computer instructions or executable code executable by the processors 24, 26, 28, 30, 32, 34 and stored in the memories 36, 38, 40, 42, 44, 46. In the depicted embodiment, the user 48 may create (block 226) the profile 200, for example, via the GUI of the NDT devices 12, 14, 16, 18, 20, 22. For example, the user 48 may navigate through a series of screens useful in entering the various parameters corresponding to the sections 202-220. In some cases, it may be desirable to customize (block 228) the profile 200 at a later time, so that user may once again navigate through one or more screens to re-enter or edit parameters corresponding to one or more of the sections 202-220.

The process 224 may then communicate (block 230) the profile 200 to interested entities, such as other users 48, user groups, external systems (e.g., cloud-based systems), and/or other NDT devices 12, 14, 16, 18, 20, 22. The profile 200 may be communicated (block 230) via wireless communications, wired communications, USB memory sticks, SD cards, and the like. The process 224 may then load parameters found in the profile 200 to inspect (block 232) a variety of assets and machinery 50, 60. In this manner, the profile 200 may more easily be used to improve inspections are a variety of sites having a variety of equipment and facilities 50, 60.

Figure 15:
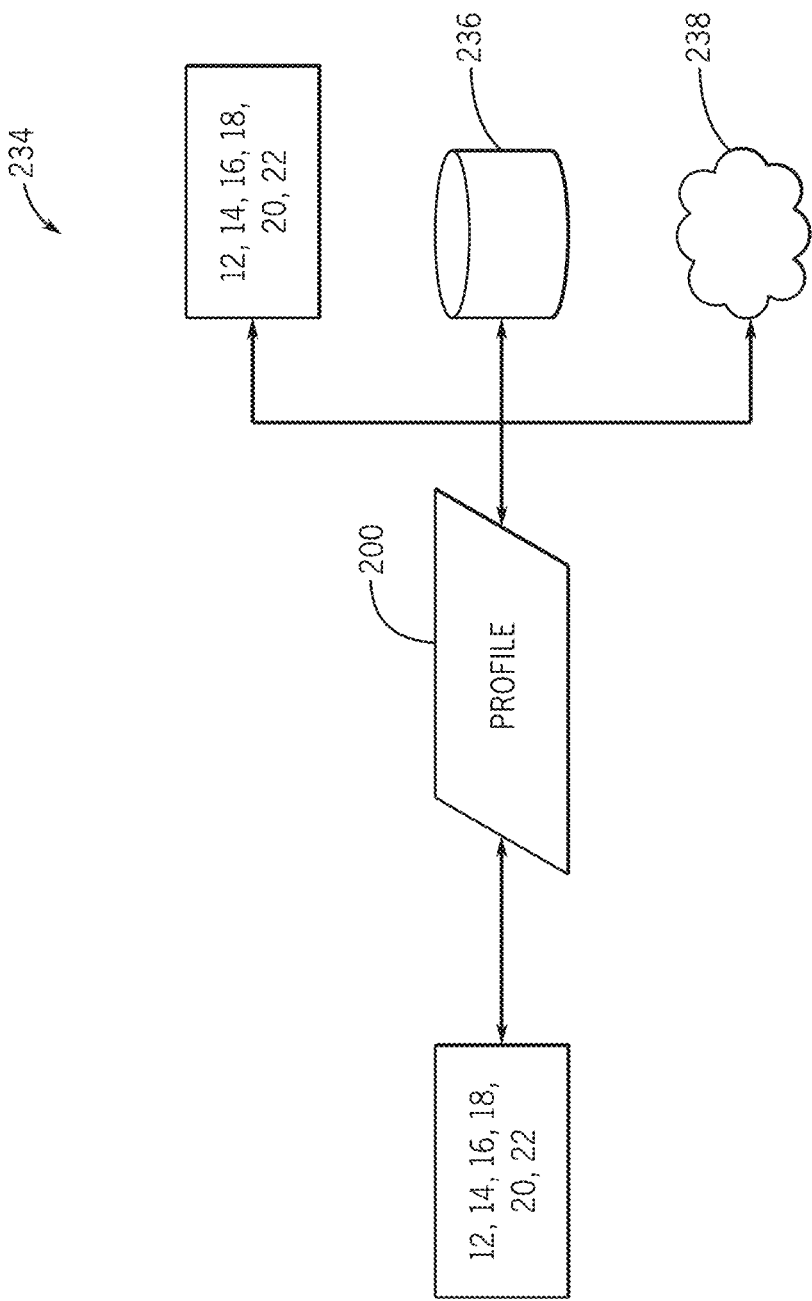
FIG. 15 is a block diagram of an embodiment of information flow showing the profile of FIG. 14 being distributed among a variety of systems, in accordance with the present embodiments.

FIG. 15 is a block diagram of an embodiment of information flow 234 showing the profile 200 being distributed among a variety of systems. As illustrated, a first NDT device 12, 14, 16, 18, 20, 22 may distribute the profile 200 to a second NDT device 12, 14, 16, 18, 20, 22, to a data repository (e.g., LAN database, WAN database) 236, to a cloud-based system, or a combination thereof. Likewise, the profile 200 may be distributed between the second device 12, 14, 16, 18, 20, 22 the data repository 236, and/or the cloud-based system back to the first NDT device 12, 14, 16, 18, 20, 22 for example, after modifying the profile 200 to further customize the profile 200. Additionally, the profile 200 may be distributed between the second NDT device 12, 14, 16, 18, 20, 22 the data repository 236, and the cloud-based system. Indeed, the profile 200 may be distribute amongst the NDT devices 12, 14, 16, 18, 20, 22 the data repository 236, and the cloud-based systems, so that the profile 200 may be applied to a variety of assets and systems 50, 60.

Technical effects of the present embodiments relate to a non-destructive testing (NDT) device (e.g., video borescope) useful in presenting and configuring selectable buttons (e.g., soft key buttons and/or virtual buttons) as part of a user-configurable GUI. In certain embodiments, the NDT device may provide, for example, one or more default rows of dynamic selectable buttons (e.g., touch buttons) to allow a select number of user-performed monitoring functions to be prioritized via a display of the NDT device. In other embodiments, due to the various applications the NDT device may be used for, the NDT device may also provide a different arrangement of monitoring functions for each monitoring state (e.g., each individual monitoring screen such as live video state or screen, a freeze-frame state or screen, a recall state or screen, and so forth) of the GUI presented on the display of the NDT device. Furthermore, in certain embodiments, the selectable buttons (e.g., soft key buttons and/or touch buttons) that appear within each screen of the GUI on the display of the NDT device may be completely user-configurable and stored as user profile or specific machine profile as the frequently or periodically uses the NDT device. In this way, by providing the NDT device with a monitoring state-based or user-configurable GUI, the user (e.g., operator, technician, engineer, and so forth) may be able to navigate through the GUI more comfortably and efficiently, thus facilitating and improving the use and user-friendliness of such devices in various monitoring applications.

Further technical effects include the creation of a profile suitable for applying a variety of parameters to the NDT device to customize the NDT device to a particular user, user group, NDT device type, specific NDT device, asset type, specific asset, component type, specific component, workflow, and menu driven inspection (MDI). The profile may include system settings, screen and display settings, connectivity settings, image and video settings, and/or measurement and annotation settings. The profile may be distributed between NDT device and data repositories, external systems, or a combination thereof.

Systems, software, and methods for profile embodiments are as follows:

1. A system, comprising:
    a non-destructive testing (NDT) device, comprising:
       a processor; and
       a computer-readable storage configured to store a profile suitable for configuring the NDT device for an inspection, wherein the processor is configured to:
          receive imaging data captured via a sensor of the NDT device;
          cause a display of the NDT device to display an image to be viewed based on the imaging data;
          create the profile based on a first user input;
          customize a setting of the NDT device based on the profile to reconfigure operations of the NDT device for the inspection; and
          distribute the profile to an external system.
2. The system of claim 1, wherein the profile comprises system settings, screen and display settings, connectivity settings, image and video settings, measurement and annotation settings, or a combination thereof.
3. The system of claim 1, wherein the profile is associated with a first user of the NDT device.
4. The system of claim 3, comprising a second profile, wherein the second profile is associated with a second user of the NDT device and not with the first user.
5. The system of claim 1, wherein the profile comprises an asset section configured to associate the profile with a specific asset, a workflow section configured to associate the profile with a specific workflow, or a combination thereof.
6. The system of claim 5, wherein the asset section comprises a component section configured to associate the profile with a subsystem of the asset.
7. The system of claim 5, wherein the workflow section comprises a menu driven inspection section configured to associate the profile with a plurality of inspection steps.
8. The system of claim 1, wherein the processor is configured to distribute the profile to a second NDT device.
9. The system of claim 1, wherein the processor is configured to receive a second profile from the external device.
10. The system of claim 1, wherein the NDT device comprises a borescope, a transportable pan-tilt-zoom camera, an eddy current device, an x-ray inspection device, an ultrasonic inspection device, or any combination thereof.
11. A tangible, non-transitory, computer readable medium, comprising computer readable instructions configured to:
    receive imaging data captured via a sensor of an NDT device;
    cause a display of the NDT device to display an image to be viewed based on the imaging data;
    create the profile based on a first user input;
    customize a setting of the NDT device based on the profile to reconfigure operations of the NDT device for an inspection; and
    distribute the profile to an external system.
12. The computer readable medium of claim 1, wherein the profile comprises system settings, screen and display settings, connectivity settings, image and video settings, measurement and annotation settings, or a combination thereof.
13. The computer readable medium of claim 1, wherein the profile comprises an asset section configured to associate the profile with a specific asset, a workflow section configured to associate the profile with a specific workflow, or a combination thereof.
14. The computer readable medium of claim 13, wherein the workflow section comprises a menu driven inspection section configured to associate the profile with a plurality of inspection steps.
15. The computer readable medium of claim 1, wherein the instructions are configured to distribute the profile to a second NDT device.
16. A method, comprising:
    receiving imaging data captured via a sensor of an NDT device;
    causing a display of the NDT device to display an image to be viewed based on the imaging data;
    creating the profile based on a first user input;
    customizing a setting of the NDT device based on the profile to reconfigure operations of the NDT device for an inspection; and
    associating the profile with a user of the NDT device.
17. The method of claim 16, comprising distributing the profile to a second NDT device, to an external system, or a combination thereof.
18. The method of claim 16, wherein the profile comprises system settings, screen and display settings, connectivity settings, image and video settings, measurement and annotation settings, or a combination thereof.
19. The method of claim 16, wherein the profile comprises an asset section configured to associate the profile with a specific asset, a workflow section configured to associate the profile with a specific workflow, or a combination thereof.
20. The method of claim 19, wherein the workflow section comprises a menu driven inspection section configured to associate the profile with a plurality of inspection steps.

Systems, software, and methods for state-based selectable buttons embodiments are as follows:

1. A system, comprising:
    a portable non-destructive testing (NDT) device, comprising:
       a processor configured to:
          receive imaging data captured via a sensor of the NDT device;

cause a display of the NDT device to display an image to be analyzed based on the imaging data;
cause the display to display a graphical user interface (GUI), wherein the GUI comprises a first plurality of user-selectable objects, and wherein each of the first plurality of user-selectable objects is configured to activate one or more monitoring functions of the NDT device; and
cause the display to display at least a first set of the first plurality of user-selectable objects, wherein the first set of the first plurality of user-selectable objects is configured to substantially overlay the image, and wherein the first set of the first plurality of user-selectable objects is displayed based at least in part on an inspection state of the NDT device.

2. The system of claim 1, wherein the portable NDT device comprises a video borescope, a portable eddy current inspection device, a transportable radiography device, a portable ultrasonic flaw detector, a transportable pan-tilt-zoom (PTZ) camera, an NDT tablet interface device, or any combination thereof.

3. The system of claim 1, wherein the display comprises a touch sensitive display, and wherein the first plurality of user-selectable objects comprises a plurality of virtual touch buttons.

4. The system of claim 1, wherein the first set of the first plurality of selectable objects comprises a first row of user-selectable graphical buttons.

5. The system of claim 4, comprising a second set of the first plurality of selectable objects, wherein the second set of the first plurality of selectable objects comprises a second row of user-selectable graphical buttons sequenced based at least in part on the inspection state of the NDT device.

6. The system of claim 5, wherein the GUI comprises a selectable switch, and wherein the processor is configured to cause the display to switch between displaying the first row of user-selectable graphical buttons to displaying the second row of user-selectable graphical buttons when the selectable switch is actuated.

7. The system of claim 1, wherein the processor is configured to receive a user indication to reconfigure the sequence of the first plurality of user-selectable objects via the display.

8. The system of claim 1, wherein the processor is configured to sequence the first plurality of user-selectable objects based at least in part on whether the GUI is in a live video monitoring state, a freeze-frame monitoring state, or in a recall monitoring state.

9. The system of claim 8, wherein, in the live video monitoring state, the processor is configured to cause the display to display a real-time or near real-time video image, wherein, in the freeze-frame monitoring state, the processor is configured to cause the display to display a still image, and wherein, in the recall monitoring state, the processor is configured to cause the display to display one or more stored video images or still images.

10. The system of claim 1, wherein the processor is configured to cause the display to display a second plurality of user-selectable objects upon detection of a selection of at least one of the user-selectable object of the first plurality of user-selectable objects.

11. The system of claim 1, wherein the NDT device is configured to inspect a turbine, a compressor, a generator, a motor, or any combination thereof.

12. A non-transitory computer-readable medium having computer executable code stored thereon, the code comprising instructions to:

receive image data captured via a camera of an NDT device;
display an image to be analyzed based on the captured image data;
display a graphical user interface (GUI), wherein the GUI comprises a plurality of user-selectable buttons, and wherein each of the plurality of user-selectable buttons is configured to execute one or more monitoring functions of the NDT device; and
display a first set of the plurality of user-selectable buttons, wherein the first set of the plurality of user-selectable buttons is configured to substantially overlay the image, and wherein the first set of the plurality of user-selectable buttons is sequenced based at least in part on a monitoring state of the GUI.

13. The non-transitory computer-readable medium of claim 12, wherein the code comprises instructions to receive a user indication to reconfigure the sequence of the plurality of user-selectable buttons.

14. The computer readable medium of claim 12, wherein the code comprises instructions to display a user-selectable switch and to switch between displaying a first row of user-selectable buttons of the plurality of user-selectable buttons to displaying a second row of user-selectable buttons of the plurality of user-selectable buttons when the selectable switch is actuated.

15. The non-transitory computer-readable medium of claim 12, wherein the code comprises instructions to sequence the plurality of user-selectable buttons based at least in part on whether the GUI is in a live video monitoring state, a freeze-frame monitoring state, or a recall monitoring state.

16. The non-transitory computer-readable medium of claim 12, wherein the code comprises instructions to display a second plurality of user-selectable buttons upon detection of a user selection of at least one user-selectable button of the plurality of user-selectable buttons.

17. A method, comprising:
receiving image data captured via a camera of an NDT device;
displaying an image to be analyzed based on the captured image data;
displaying a graphical user interface (GUI), wherein the GUI comprises a plurality of graphical touch buttons, and wherein each of the plurality of graphical touch buttons is configured to execute one or more monitoring functions of the NDT device; and
displaying a first set of the plurality of graphical touch buttons, wherein the first set of the plurality of graphical touch buttons is configured to substantially overlay the image, and wherein the first set of the plurality of graphical touch buttons is sequenced based at least in part on a monitoring state of the GUI.

18. The method of claim 17, wherein the first plurality of graphical touch buttons comprises a first row of at least four graphical touch buttons and the second plurality of graphical touch buttons comprises a second row of at least four graphical touch buttons, and wherein a sequence or configuration of the presentation of the first plurality of graphical touch buttons and the second plurality of graphical touch is user-configurable.

19. The method of claim 17, wherein the GUI comprises a graphical touch switch displayed along with at least one of the first plurality of graphical touch buttons and the second plurality of graphical touch buttons, and wherein the GUI is configured to present the first plurality of graphical touch buttons when the graphical touch switch is in a first position and to present the second plurality of graphical touch buttons when the graphical touch switch is in a second position.

20. The method of claim 17, wherein the plurality of states of the GUI comprises a live video monitoring state, a freeze-frame monitoring state, or a recall monitoring state.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A system, comprising:
a portable non-destructive testing (NDT) device, comprising:
a processor configured to:
receive imaging data captured via a sensor of the NDT device;
cause a display of the NDT device to display an image to be analyzed based on the imaging data;
cause the display to display a graphical user interface (GUI), wherein the GUI comprises a first plurality of user-selectable objects, and wherein each of the first plurality of user-selectable objects is configured to activate one or more monitoring functions of the NDT device; and
cause the display to display at least a first set of the first plurality of user-selectable objects, wherein the first set of the first plurality of user-selectable objects is configured to substantially overlay the image, and wherein the first set of the first plurality of user-selectable objects is displayed based at least in part on an inspection state of the NDT device, wherein the display comprises a touch sensitive display, and wherein the first plurality of user-selectable objects comprises a first plurality of virtual touch buttons sequenced based at least in part on the inspection state, on the touch sensitive display, wherein the inspection state comprises a visual image state displaying the image captured during inspection, and wherein the processor is configured to store a user-configurable sequence of the presentation of the first plurality of virtual touch buttons in a user profile corresponding to a specific user of the NDT device.

2. The system of claim 1, wherein the portable NDT device comprises a video borescope, a portable eddy current inspection device, a transportable radiography device, a portable ultrasonic flaw detector, a transportable pan-tilt-zoom (PTZ) camera, an NDT tablet interface device, or any combination thereof.

3. The system of claim 1, wherein the first set of the first plurality of selectable objects comprises a first row of user-selectable graphical buttons.

4. The system of claim 3, comprising a second set of the first plurality of selectable objects, wherein the second set of the first plurality of selectable objects comprises a second row of user-selectable graphical buttons sequenced based at least in part on the visual image state of the NDT device.

5. The system of claim 4, wherein the GUI comprises a selectable switch, and wherein the processor is configured to cause the display to switch between displaying the first row of user-selectable graphical buttons to displaying the second row of user-selectable graphical buttons on a same screen when the selectable switch is actuated.

6. The system of claim 1, wherein the processor is configured to receive a user indication to reconfigure the sequence of the first plurality of user-selectable objects via the display.

7. The system of claim 1, wherein the visual image state comprises a live video monitoring state, a freeze-frame monitoring state, or in a recall monitoring state.

8. The system of claim 7, wherein, in the live video monitoring state, the processor is configured to cause the display to display a real-time or near real-time video image, wherein, in the freeze-frame monitoring state, the processor is configured to cause the display to display a still image, and wherein, in the recall monitoring state, the processor is configured to cause the display to display one or more stored video images or still images.

9. The system of claim 1, wherein the processor is configured to cause the display to display a second plurality of virtual touch buttons upon detection of a selection of at least one of the user-selectable object of the first plurality of user-selectable objects.

10. The system of claim 1, wherein the NDT device is configured to inspect a turbine, a compressor, a generator, a motor, or any combination thereof.

11. A non-transitory computer-readable medium having computer executable code stored thereon, the code comprising instructions to:
receive image data captured via a camera of an NDT device;
display an image to be analyzed based on the captured image data;
display a graphical user interface (GUI), wherein the GUI comprises a plurality of user-selectable buttons, and wherein each of the plurality of user-selectable buttons is configured to execute one or more monitoring functions of the NDT device;
display a first set of the plurality of user-selectable buttons, wherein the first set of the plurality of user-selectable buttons is configured to substantially overlay the image, and wherein the first set of the plurality of user-selectable buttons is sequenced based at least in part on a monitoring state of the GUI, wherein the monitoring state comprises a visual image state displaying the image to be analyzed, and;
store, in the NDT device, a user-configurable sequence of the presentation of the first set of the plurality of user-selectable buttons in a user profile corresponding to a specific user of the NDT device.

12. The non-transitory computer-readable medium of claim 11, wherein the code comprises instructions to receive a user indication to reconfigure the sequence of the plurality of user-selectable buttons.

13. The computer readable medium of claim 11, wherein the code comprises instructions to display a user-selectable switch and to switch between displaying a first row of user-selectable buttons of the plurality of user-selectable buttons to displaying a second row of user-selectable buttons of the plurality of user-selectable buttons on a same screen when the selectable switch is actuated.

14. The non-transitory computer-readable medium of claim 11, wherein the visual image state comprises a live video monitoring state, a freeze-frame monitoring state, or a recall monitoring state.

15. The non-transitory computer-readable medium of claim 11, wherein the code comprises instructions to display a second plurality of user-selectable buttons upon detection of a user selection of at least one user-selectable button of the plurality of user-selectable buttons.

16. A method, comprising:
receiving image data captured via a camera of an NDT device;
displaying an image to be analyzed based on the captured image data;
displaying a graphical user interface (GUI), wherein the GUI comprises a plurality of graphical touch buttons, and wherein each of the plurality of graphical touch buttons is configured to execute one or more monitoring functions of the NDT device;
displaying a first set of the plurality of graphical touch buttons, wherein the first set of the plurality of graphical touch buttons is configured to substantially overlay the image, and wherein the first set of the plurality of graphical touch buttons is sequenced based at least in part on a monitoring state of the GUI, wherein the monitoring state comprises a visual image displaying the image to be analyzed; and
storing, in the NDT device, a user-configurable sequence of the presentation of the first plurality of graphical touch buttons, the second plurality of touch buttons, or the combination thereof, in a user profile corresponding to a specific user of the NDT device.

17. The method of claim 16, wherein the first plurality of graphical touch buttons comprises a first row of at least four graphical touch buttons and the second plurality of graphical touch buttons comprises a second row of at least four graphical touch buttons, and wherein a sequence or configuration of the presentation of the first plurality of graphical touch buttons and the second plurality of graphical touch buttons is user-configurable.

18. The method of claim 16, wherein the GUI comprises a graphical touch switch displayed along with at least one of the first plurality of graphical touch buttons and the second plurality of graphical touch buttons, and wherein the GUI is configured to present the first plurality of graphical touch buttons when the graphical touch switch is in a first position and to present the second plurality of graphical touch buttons when the graphical touch switch is in a second position.

19. The method of claim 16, wherein the visual image state comprises a live video monitoring state, a freeze-frame monitoring state, or a recall monitoring state.

* * * * *